(12) United States Patent
Daubs et al.

(10) Patent No.: US 9,161,788 B2
(45) Date of Patent: Oct. 20, 2015

(54) ROD REDUCER APPARATUS FOR SPINAL CORRECTIVE SURGERY

(75) Inventors: Michael Daubs, Las Vegas, NV (US); David Rathbun, West Chester, PA (US); Brian Dec, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 861 days.

(21) Appl. No.: 13/139,373

(22) PCT Filed: Dec. 8, 2009

(86) PCT No.: PCT/US2009/006433
§ 371 (c)(1),
(2), (4) Date: Feb. 9, 2012

(87) PCT Pub. No.: WO2010/077284
PCT Pub. Date: Jul. 8, 2010

(65) Prior Publication Data
US 2012/0271365 A1 Oct. 25, 2012

Related U.S. Application Data

(60) Provisional application No. 61/138,392, filed on Dec. 17, 2008.

(51) Int. Cl.
*A61B 17/70* (2006.01)

(52) U.S. Cl.
CPC ......... *A61B 17/7086* (2013.01); *A61B 17/7085* (2013.01)

(58) Field of Classification Search
CPC ................... A61B 17/7085; A61B 17/7086
USPC .............................................. 606/86 A, 86 R
See application file for complete search history.

(56) References Cited

U.S. PATENT DOCUMENTS

| 5,910,141 A | 6/1999 | Morrison et al. |
| 7,470,279 B2 * | 12/2008 | Jackson ........................ 606/300 |
| 7,491,218 B2 * | 2/2009 | Landry et al. .................. 606/246 |
| 7,563,264 B2 * | 7/2009 | Landry et al. ................ 606/86 A |
| 7,621,918 B2 * | 11/2009 | Jackson ....................... 606/86 A |

(Continued)

FOREIGN PATENT DOCUMENTS

| EP | 1574175 | 9/2005 |
| WO | WO 2006/036324 | 4/2006 |

(Continued)

*Primary Examiner* — Eduardo C Robert
*Assistant Examiner* — Stuart S Bray
(74) *Attorney, Agent, or Firm* — Baker & Hostetler LLP (57) ABSTRACT

Spinal rod reduction apparatuses, systems, and methods are provided. In various examples, a rod reduction apparatus includes a first threaded member (130, 210, 330) including an engagement feature (138A, 138B, 220, 332, 334) configured to selectively anchor the first threaded member to the implantable screw assembly. A second threaded member (110, 230, 310) is configured to threadably engage with the first threaded member. The second threaded member is axially movable with respect to the first threaded member with rotation of the second threaded member. A spinal rod urging member (120, 240, 320) is axially movable with the second threaded member. The urging member includes a bearing surface (126, 242, 320) that is configured to selectively abut the spinal rod and selectively urge the spinal rod toward the implantable screw assembly with rotation of the second threaded member in a first rotational direction.

33 Claims, 11 Drawing Sheets

(56) References Cited

U.S. PATENT DOCUMENTS

| | | | |
|---|---|---|---|
| 7,651,502 B2 * | 1/2010 | Jackson | 606/99 |
| 7,666,188 B2 * | 2/2010 | Anderson et al. | 606/104 |
| 7,666,189 B2 * | 2/2010 | Gerber et al. | 606/104 |
| 7,909,835 B2 * | 3/2011 | Oribe et al. | 606/104 |
| 7,922,727 B2 * | 4/2011 | Songer et al. | 606/86 A |
| 8,034,084 B2 * | 10/2011 | Landry et al. | 606/265 |
| 8,048,129 B2 * | 11/2011 | Forton et al. | 606/279 |
| 8,066,739 B2 * | 11/2011 | Jackson | 606/246 |
| 8,075,592 B2 * | 12/2011 | Landry et al. | 606/246 |
| 8,100,915 B2 * | 1/2012 | Jackson | 606/86 A |
| 8,152,810 B2 * | 4/2012 | Jackson | 606/86 A |
| 8,162,948 B2 * | 4/2012 | Jackson | 606/86 A |
| 8,202,274 B2 * | 6/2012 | McLean | 606/86 A |
| 8,206,394 B2 * | 6/2012 | Stad et al. | 606/86 A |
| RE43,526 E * | 7/2012 | Morrison et al. | 606/86 A |
| 8,273,089 B2 * | 9/2012 | Jackson | 606/86 A |
| 8,292,892 B2 * | 10/2012 | Jackson | 606/86 A |
| 8,366,714 B2 * | 2/2013 | Jones et al. | 606/86 A |
| 8,377,067 B2 * | 2/2013 | Jackson | 606/86 A |
| 8,394,108 B2 * | 3/2013 | McLean et al. | 606/104 |
| 8,414,588 B2 * | 4/2013 | Stad et al. | 606/86 A |
| 8,439,922 B1 * | 5/2013 | Arnold et al. | 606/86 A |
| 8,439,924 B1 * | 5/2013 | McBride et al. | 606/86 A |
| 8,496,685 B2 * | 7/2013 | Landry et al. | 606/246 |
| 8,523,873 B2 * | 9/2013 | Bharadwaj et al. | 606/96 |
| 8,540,718 B2 * | 9/2013 | Dauster et al. | 606/86 A |
| 8,551,141 B2 * | 10/2013 | Gephart et al. | 606/246 |
| 8,591,515 B2 * | 11/2013 | Jackson | 606/86 A |
| 8,608,746 B2 * | 12/2013 | Kolb et al. | 606/86 A |
| 8,641,719 B2 * | 2/2014 | Gephart et al. | 606/86 A |
| 8,657,825 B2 * | 2/2014 | Justis et al. | 606/86 A |
| 8,672,944 B2 * | 3/2014 | Boachie-Adjei et al. | 606/86 A |
| 2002/0058950 A1 * | 5/2002 | Winterbottom et al. | 606/99 |
| 2004/0147936 A1 | 7/2004 | Rosenberg et al. | |
| 2006/0074418 A1 * | 4/2006 | Jackson | 606/61 |
| 2006/0095035 A1 | 5/2006 | Jones et al. | |
| 2006/0247630 A1 * | 11/2006 | Iott et al. | 606/61 |
| 2007/0213722 A1 * | 9/2007 | Jones et al. | 606/61 |
| 2008/0119852 A1 | 5/2008 | Dalton et al. | |
| 2011/0144695 A1 * | 6/2011 | Rosenberg et al. | 606/264 |
| 2011/0172714 A1 * | 7/2011 | Boachie-Adjei et al. | 606/264 |
| 2011/0257692 A1 * | 10/2011 | Sandstrom et al. | 606/86 A |
| 2012/0215266 A1 * | 8/2012 | Jones | 606/86 A |
| 2014/0343613 A1 * | 11/2014 | Eliasen et al. | 606/278 |

FOREIGN PATENT DOCUMENTS

| | | |
|---|---|---|
| WO | WO 2006036324 A2 * | 4/2006 |
| WO | WO 2006036324 A3 * | 3/2007 |
| WO | WO 2008/070442 | 6/2008 |
| WO | WO 2010/077284 | 7/2010 |

* cited by examiner

ROD REDUCER APPARATUS FOR SPINAL CORRECTIVE SURGERY

CROSS-REFERENCE TO RELATED APPLICATIONS

This application is the National Stage of International Application No. PCT/US2009/006433, filed Dec. 8, 2009, which claims the benefit of U.S. Provisional Application No. 61/138,392, filed Dec. 17, 2008, the disclosures of which are incorporated herein by reference in their entireties for all purposes.

TECHNICAL FIELD

This patent document pertains generally to orthopedics. More particularly, but not by way of limitation, this patent document pertains to an apparatus and method for spinal deformity correction.

BACKGROUND

Several techniques exist in the field of spinal surgery for reducing a spinal rod into a posterior pedicle screw. The primary technique utilizes a separate rod reduction instrument that couples to the head of the screw after the screw is inserted and the rod is placed, such as rocker forks or ratchet style instruments, which are designed to reduce the rod one level at a time, i.e., to each pedicle screw separately. Such segmental reduction techniques may produce large axial loads on the pedicle screws.

Alternatively, a rod can be conformed to a specific deformity and then seated within an implanted pedicle screw. Once seated, the deformity can be corrected by bending the rod in situ. This technique may be time-consuming and places stresses and strains on the rod prior to implantation.

Certain rod reduction techniques utilize specialty reduction pedicle screws that include integrated upwardly extending tabs that can be used to reduce the rod gradually over the entire length of a deformity. Once the rod reduction is completed, the extended tabs are broken off. This technique, however, is typically limited to the reduction screw only and can cause the implant to be expensive.

OVERVIEW

The present inventors have recognized, among other things, that stresses and strains to pedicle screws and/or spinal rods present problems during spinal rod reduction procedures. The present inventors have further recognized that there exists an unmet need for a streamlined, externally mounted mini-reduction instrument that can be used on any hook or screw type, including monoaxial, polyaxial, and sagittal screws, and can be reused, modified, or removed as necessary at any time during the entire course of the spinal corrective procedure.

This patent document describes, among other things, apparatuses, systems, and methods for spinal rod reduction. In various examples, a rod reduction apparatus includes a first threaded member including an engagement feature configured to selectively anchor the first threaded member to the implantable screw assembly. A second threaded member is configured to threadably engage with the first threaded member. The second threaded member is axially movable with respect to the first threaded member with rotation of the second threaded member. A spinal rod urging member is axially movable with the second threaded member. The urging member includes a bearing surface that is configured to selectively abut the spinal rod and selectively urge the spinal rod toward the implantable screw assembly with rotation of the second threaded member in a first rotational direction.

In Example 1, an apparatus is configured to selectively engage with a spinal rod and an implantable screw assembly. The apparatus comprises a first threaded member including first threads around at least a portion of an outer surface of the first threaded member. The first threaded member includes an engagement feature configured to selectively anchor the first threaded member to the implantable screw assembly. A second threaded member includes second threads around at least a portion of an inner surface of the second threaded member. The second threaded member is configured to threadably engage with the first threaded member. The second threaded member is axially movable with respect to the first threaded member with rotation of the second threaded member. A spinal rod urging member is axially movable with the second threaded member. The urging member includes a bearing surface that is configured to selectively abut the spinal rod and selectively urge the spinal rod toward the implantable screw assembly with rotation of the second threaded member in a first rotational direction.

In Example 2, the apparatus of Example 1 optionally is configured such that the engagement feature includes at least one protrusion configured to mate with a corresponding number of receptacles of the implantable screw assembly.

In Example 3, the apparatus of one or more of Examples 1-2 optionally is configured such that the engagement feature includes a grasping element configured to selectively couple to a proximal end of the implantable screw assembly.

In Example 4, the apparatus of one or more of Examples 1-3 optionally is configured such that the engagement feature is disposed at a distal end of the first threaded member.

In Example 5, the apparatus of one or more of Examples 1-4 optionally is configured such that the urging member is coupled to the second threaded member.

In Example 6, the apparatus of one or more of Examples 1-5 optionally is configured such that the first threaded member is substantially tubular and includes a first leg and a second leg, the first and second legs extending substantially axially, wherein distal ends of the first and second legs are configured to be selectively radially separable.

In Example 7, the apparatus of Example 6 optionally is configured such that the first and second legs are substantially semi-circular in cross section.

In Example 8, the apparatus of Example 7 optionally is configured such that the first and second legs of the first threaded member are held together by the second threaded member threadably engaged around the outer surface of the first threaded member.

In Example 9, the apparatus of Example 8 optionally is configured such that the outer surface of the first threaded member includes a portion of decreased diameter configured to allow the first and second legs to selectively radially separate with the first threaded member threadably engaged with the second threaded member.

In Example 10, the apparatus of one or more of Examples 6-9 optionally is configured such that the first threaded member includes a gap between the first leg and the second leg, the gap being configured to accommodate the spinal rod.

In Example 11, the apparatus of Example 10 optionally is configured such that the bearing surface of the urging member is disposed at least partially within the gap between the first leg and the second leg.

In Example 12, the apparatus of one or more of Examples 1-11 optionally is configured such that the second threaded member includes a tool engagement portion configured to engage with a tool configured to rotate the second threaded member with respect to the first thread member.

In Example 13, the apparatus of Example 12 optionally is configured such that the tool engagement portion includes a recess including a drive surface configured to mate with the tool.

In Example 14, the apparatus of one or more of Examples 12-13 optionally is configured such that the tool engagement portion includes a nut configured to mate with the tool.

In Example 15, the apparatus of Example 14 optionally is configured such that the nut includes a hex nut.

In Example 16, the apparatus of one or more of Examples 1-15 optionally is configured such that the spinal rod urging member includes a claw element including one or more arms, each arm including the bearing surface configured to selectively abut the spinal rod.

In Example 17, the apparatus of Example 16 optionally is configured such that the bearing surface of each arm is disposed at an end of the arm.

In Example 18, the apparatus of one or more of Examples 16-17 optionally is configured such that the bearing surface includes a rod recess.

In Example 19, the apparatus of one or more of Examples 1-18 optionally is configured such that the engagement feature of the first threaded member includes a grasping element configured to couple to an underside of a head of the implantable screw assembly.

In Example 20, the apparatus of one or more of Examples 1-19 optionally is configured such that the second threaded member includes a gripping surface configured to grip during manual rotation of the second threaded member with respect to the first threaded member.

In Example 21, an method comprises placing at least one rod reducer along a spinal rod and substantially in alignment with at least one pedicle screw. Placement of the rod reducer along the spinal rod includes substantially aligning a bearing surface of a spinal rod urging member of the rod reducer with the spinal rod. The rod reducer is engaged with the pedicle screw. The rod reducer is incrementally actuated to gradually reduce the spinal rod into engagement with the pedicle screw. Actuation of the rod reducer causes movement of the bearing surface toward the pedicle screw to urge the spinal rod toward the pedicle screw. The pedicle screw is engaged with the spinal rod.

In Example 22, the apparatus of Example 21 optionally is configured such that engaging the pedicle screw with the spinal rod includes attaching a locking cap to the pedicle screw to retain the spinal rod in engagement with the pedicle screw.

In Example 23, the apparatus of one or more of Examples 21-22 optionally comprises removing the rod reducer from the pedicle screw after engagement of the pedicle screw with the spinal rod.

In Example 24, the apparatus of Example 23 optionally comprises cleaning the rod reducer for reuse after removal of the rod reducer from the pedicle screw.

In Example 25, the apparatus of one or more of Examples 21-24 optionally is configured such that placing the at least one rod reducer along the spinal rod includes placing two or more rod reducers along the spinal rod and substantially in alignment with two or more pedicle screws.

In Example 26, the apparatus of one or more of Examples 21-25 optionally comprises placing the spinal rod along a plurality of pedicle screws. Without using a rod reducer, the spinal rod is engaged to one or more pedicle screws for which no spinal rod reduction is necessary. Using one or more rod reducers, the spinal rod is engaged to one or more pedicle screws for which spinal rod reduction is necessary.

In Example 27, the apparatus of one or more of Examples 21-26 optionally is configured such that engaging the rod reducer with the pedicle screw includes manually engaging the rod reducer with the pedicle screw.

In Example 28, the apparatus of one or more of Examples 21-27 optionally is configured such that engaging the rod reducer with the pedicle screw includes engaging the rod reducer with the pedicle screw using a tool configured to mate with a tool engagement portion of the rod reducer.

In Example 29, a spinal rod reduction system comprises a spinal rod. A plurality of pedicle screws is configured to engage with the spinal rod. A plurality of rod reducers each includes a first threaded member including first threads around at least a portion of an outer surface of the first threaded member. The first threaded member includes an engagement feature configured to selectively anchor the first threaded member to the pedicle screw. A second threaded member includes second threads around at least a portion of an inner surface of the second threaded member. The second threaded member is configured to threadably engage with the first threaded member. The second threaded member is axially movable with respect to the first threaded member with rotation of the second threaded member. A spinal rod urging member is axially movable with the second threaded member. The urging member includes a bearing surface that is configured to selectively abut the spinal rod and selectively urge the spinal rod toward the pedicle screw with rotation of the second threaded member in a first rotational direction.

In Example 30, the system of Example 29 optionally is configured such that the rod reducers are configured to engage with the pedicle screws and the spinal rod at locations where the spinal rod is spaced from the pedicle screws.

In Example 31, the system of one or more of Examples 29-30 optionally is configured such that the plurality of rod reducers are configured to incrementally urge the spinal rod toward the plurality of pedicle screws.

In Example 32, the system of one or more of Examples 29-31 optionally comprises a locking cap configured to engage with the pedicle screw and retain the spinal rod in engagement with the pedicle screw.

In Example 33, the system of one or more of Examples 29-32 optionally comprises a tool configured to mate with a tool engagement portion of each of the rod reducers, the tool being configured to rotate the second threaded member with respect to the first thread member.

In Example 34, the system of Example 33 optionally is configured such that the tool engagement portion includes a recess including a drive surface configured to mate with the tool.

In Example 35, the system of one or more of Examples 33-34 optionally is configured such that the tool engagement portion includes a nut configured to mate with the tool.

In Example 36, a spinal rod reduction assembly comprises one or more pedicle screws engaged with one or more vertebrae. A spinal rod is substantially aligned with the one or more pedicle screws. At least one rod reducer is removably engaged with at least one pedicle screw at a location where the spinal rod is spaced by a distance from the pedicle screw. The rod reducer includes a spinal rod urging member axially movable with respect to the rod reducer. The urging member includes a bearing surface that is configured to selectively abut the spinal rod and selectively urge, with actuation of the rod reducer, the spinal rod toward the pedicle screw to decrease the distance between the spinal rod and the pedicle screw.

These and other examples, advantages, and features of the present rod reduction apparatuses and methods will be set forth in part in the following Detailed Description. As such, this Overview is intended to provide an overview of subject matter of the present patent document. It is not intended to provide an exclusive or exhaustive explanation of the invention. The Detailed Description is included to provide further information about the present patent document.

BRIEF DESCRIPTION OF THE DRAWINGS

In the drawings, like numerals describe similar components throughout the several views. Like numerals having different letter suffixes represent different instances of similar components. The drawings illustrate generally, by way of example, but not by way of limitation, various embodiments discussed in the present document.

DETAILED DESCRIPTION

The present inventors have recognized, among other things, that it is desirable to construct a streamlined, externally mounted mini-reduction instrument that can be used on any hook or screw type, including monoaxial, polyaxial, and sagittal screws, and can be reused, modified, or removed as necessary at any time during the entire course of the spinal corrective procedure.

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the geometric center or orientation of the instrument assembly and related parts thereof. The words, "anterior", "posterior", "superior," "inferior", "lateral" and related words and/or phrases designate preferred positions and orientations in the human body to which reference is made and are not meant to be limiting. The terminology includes the above-listed words, derivatives thereof and words of similar import.

In reference to FIGS. 1-7, a miniature rod reducer instrument 100 in accordance with an embodiment of the present invention includes an outer drive sleeve 110, a retaining guide ring 120, and a threaded tube 130. The rod reducer 100 is selectively engageable with a spinal rod 140 and a pedicle screw assembly 150, which can assume the form of a monoaxial pedicle screw, a sagittal screw, a polyaxial pedicle screw, a hook or nearly any type of screw that includes a head or anchor seat constructed to engage a distal end of the threaded tube 130. The outer drive sleeve 110, in an example, includes a proximal end, a distal end, a longitudinal axis between the proximal and distal ends, a cannulated interior, a gripping surface 112 disposed on a proximal exterior surface that may include a knurled or other traction grip surface, a visibility window 114 that enables viewing and weight reduction, a drive surface 116 such as a hex drive disposed interior to the proximal end and a series of interior threading 118 disposed on an interior surface at the distal end. The drive surface 116, in an example, is engageable with a ratcheting T-handle driver instrument (FIG. 7) with a hex drive coupler 160 to impart additional mechanical rotational force to the outer drive sleeve 110 to assist in rod reduction.

Figure 6A:
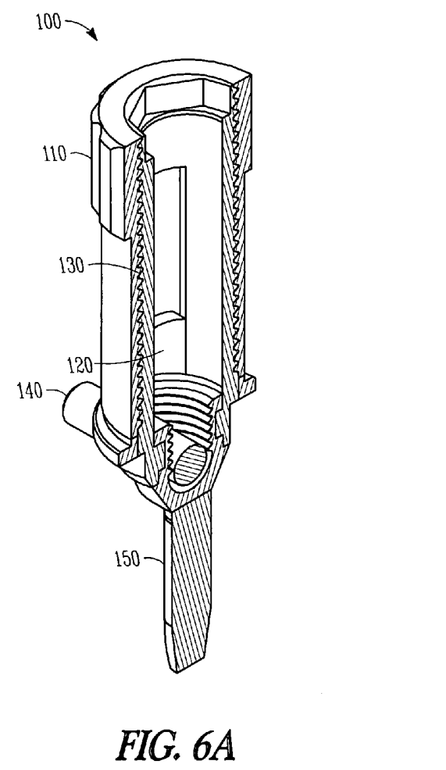
FIGS. 6A and 6B illustrate perspective, cross-sectional views taken along lines 6A-6A and 6B-6B of FIG. 5B of the rod reducer instrument of FIG. 1.
Figure 6B:
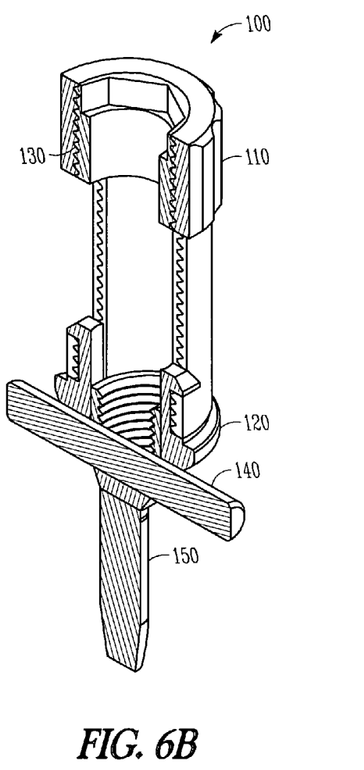
Figure 7:
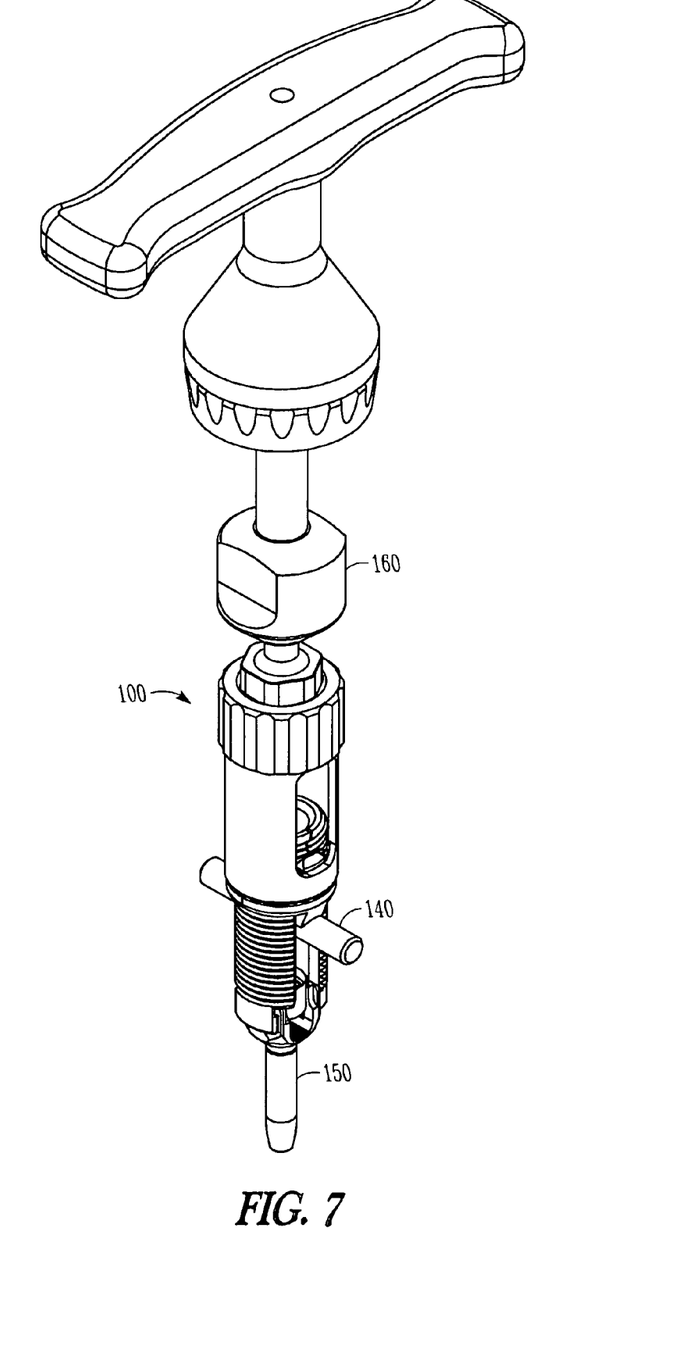
FIG. 7 illustrates a front perspective view of the rod reducer instrument of FIG. 1 coupled to a locking cap ratcheting T-handle driver instrument with a hex drive coupler, a spinal rod, and a pedicle screw assembly.
Figure 8A:
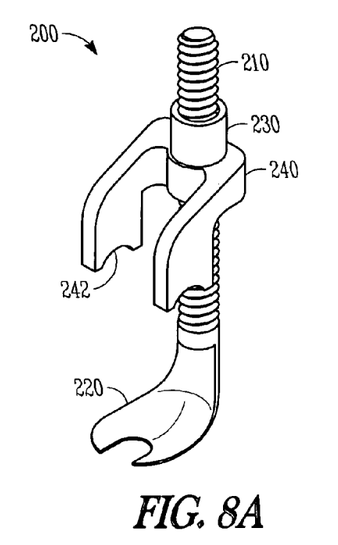
FIGS. 8A-8D illustrate various perspective views of a miniature rod reducer instrument in accordance with an embodiment of the present document.
Figure 8B:
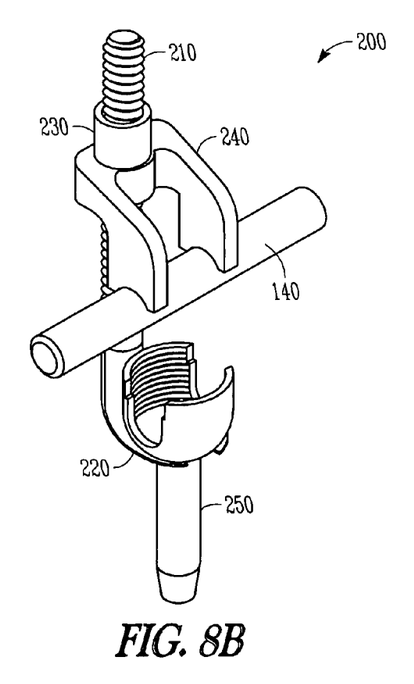
Figure 8C:
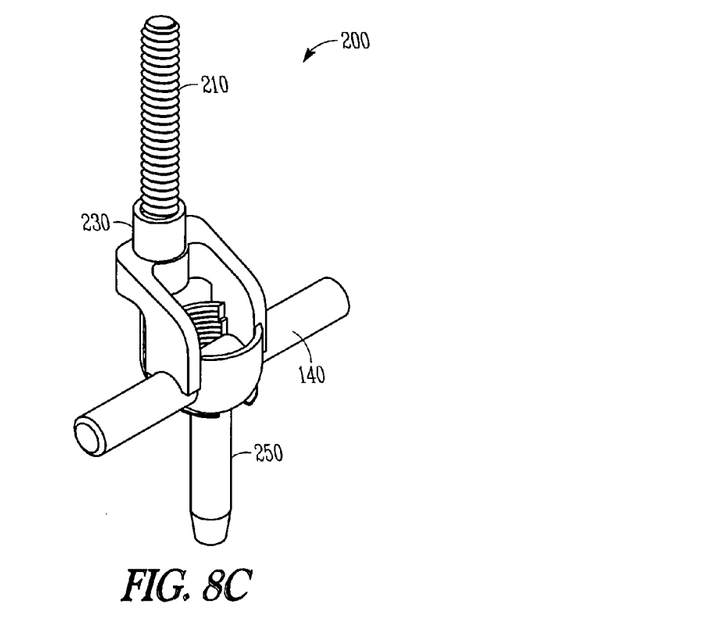
Figure 8D:
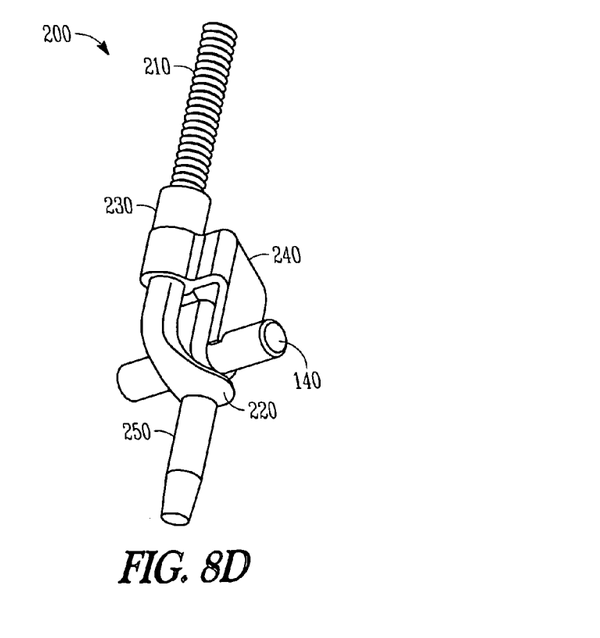
Figure 9A:
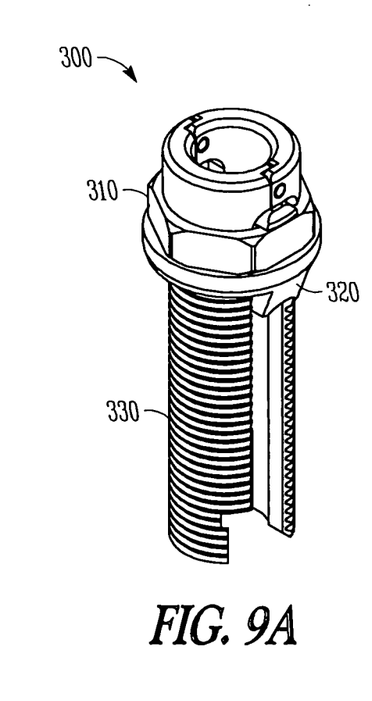
FIGS. 9A-9F illustrate various perspective views of a miniature rod reducer instrument in accordance with an embodiment of the present document.
Figure 9B:
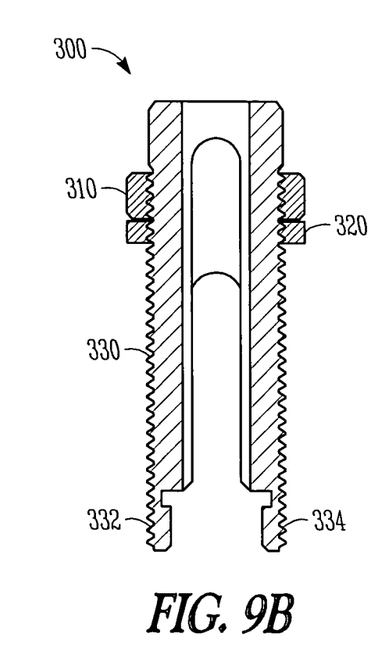
Figure 9C:
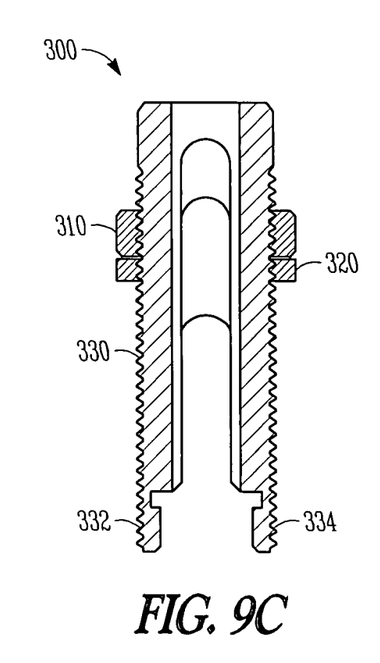
Figure 9D:
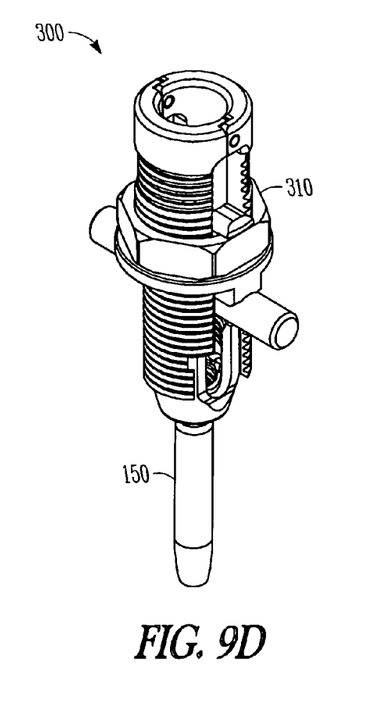
Figure 9E:
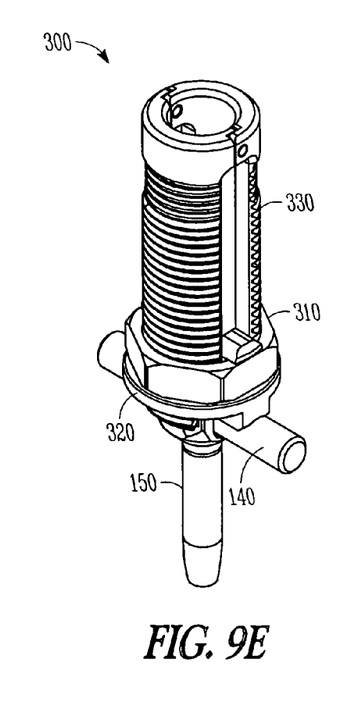
Figure 9F:
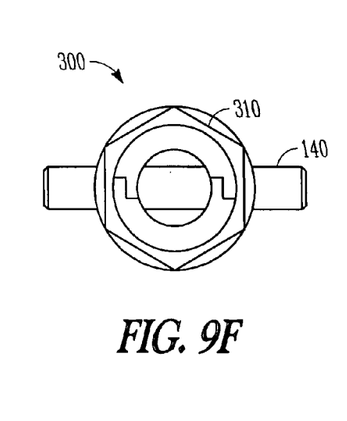

In an example, the threaded tube 130 includes a proximal end, a distal end, a longitudinal axis extending between the proximal and distal ends, a cannulated interior, a first leg 132 and a second leg 134. The first and second legs 132, 134, in an example, are held together by the interior confines of the outer drive sleeve 110 and the retaining guide ring 120. In some examples, the first leg 132 includes an exterior threading 136A and the second leg 134 includes an exterior threading 136B. The exterior threading 136A, 136B can be a single or multi-lead thread to provide for faster reduction speed. In an example, the exterior threading 136A, 136B is a two start M18×1.5 with an effective pitch of 3 mm. In some examples, the first leg 132 includes an engagement feature 138A interior to its distal end and the second leg 134 includes an engagement feature 138B interior to its distal end. The engagement features 138A, 138B selectively engage and couple to the exterior surface of a pedicle screw assembly 150. In an example, the engagement features 138A, 138B are comprised of male protrusions that mate with female receptacles inherent on the exterior surface of the pedicle screw assembly 150. The engagement features 138A, 138B and their corresponding receptacles, in an example, provide stabilization in all three axes, as is best shown in FIG. 6A. In an example, the first leg 132 includes an exteriorly disposed feature 139A near the proximal end and the second leg 134 includes an exteriorly disposed feature 139B near the proximal end. The exteriorly disposed features 139A, 139B, in an example, are comprised of regions in which the outer diameter of the threaded tube 130 and the pitch diameter of the exterior threading 136A, 136B decrease to allow the first and second arms 132, 134 to splay open slightly at the distal end to enable easy introduction of the rod reducer 100 over the pedicle screw assembly 150 and corresponding engagement of the engagement features 138A, 138B with the receptacles of the pedicle screw assembly 150. The first and second arms 132, 134 are configured to splay open at the distal end approximately 2.5 degrees in an example.

Figure 1A:
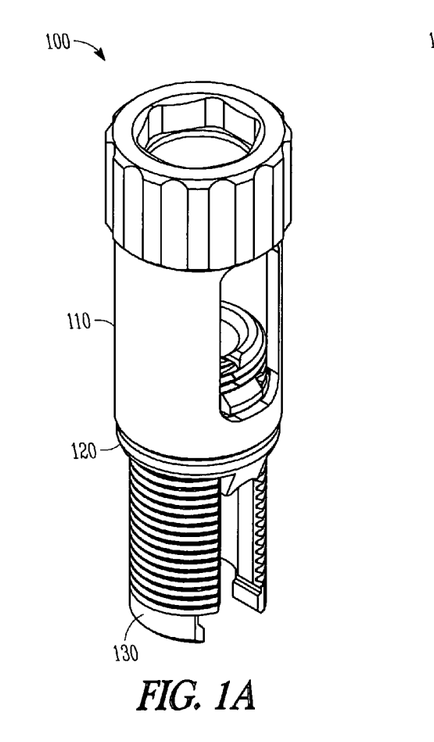
FIGS. 1A and 1B illustrate a front perspective view and a front elevational view, respectively, of a miniature rod reducer instrument in accordance with an embodiment of the present document.
Figure 1B:
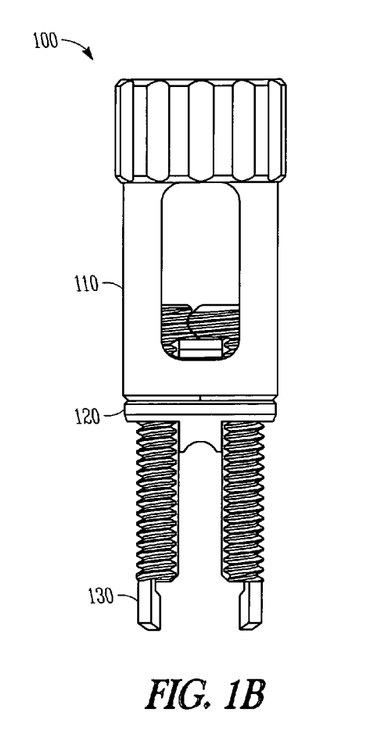
Figure 2A:
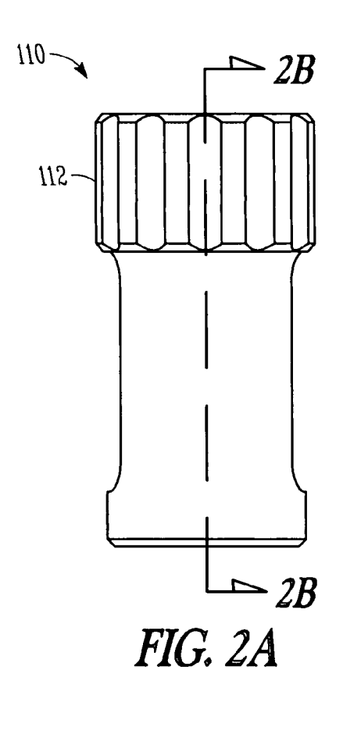
FIGS. 2A, 2B, and 2C illustrate a side elevational view, a cross-sectional view taken along line 2B-2B of FIG. 2A, and a top plan view, respectively, of an outer drive sleeve element of the miniature rod reducer instrument of FIG. 1.
Figure 2B:
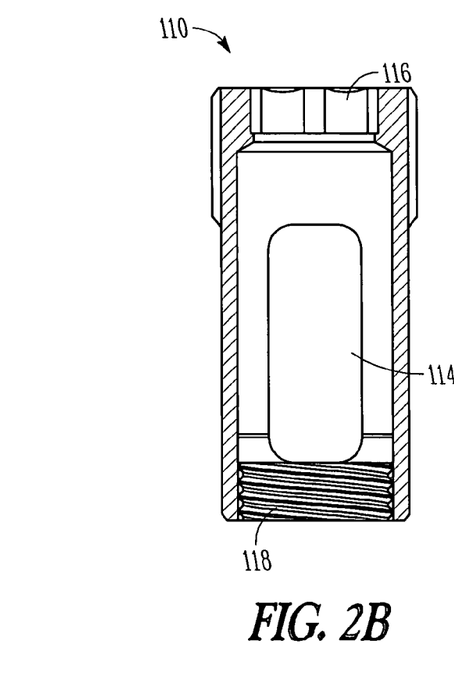
Figure 2C:
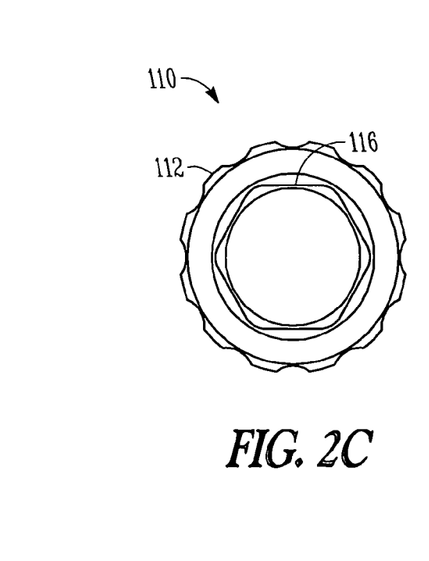
Figure 3A:
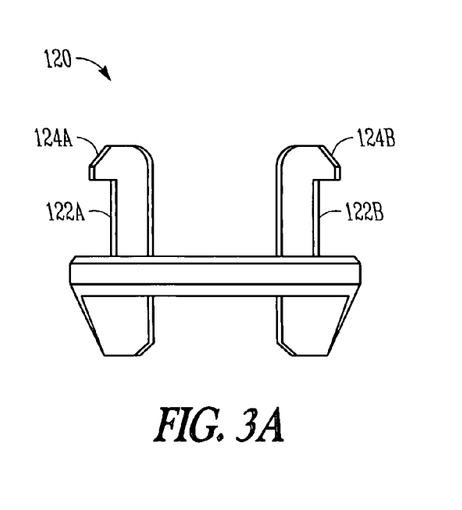
FIGS. 3A, 3B, and 3C illustrate a front elevational view, a left side elevational view, and a top plan view, respectively, of a retaining guide ring element of the miniature rod reducer instrument of FIG. 1.
Figure 3B:
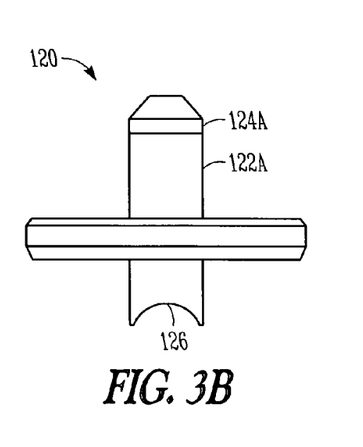
Figure 3C:
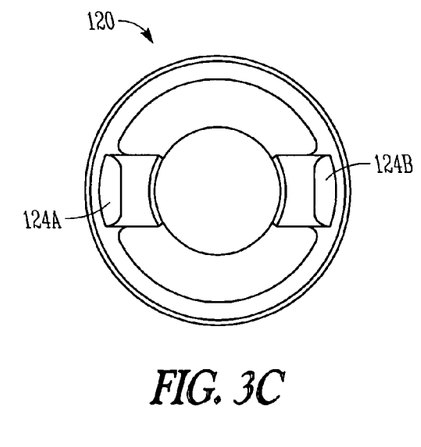
Figure 4A:
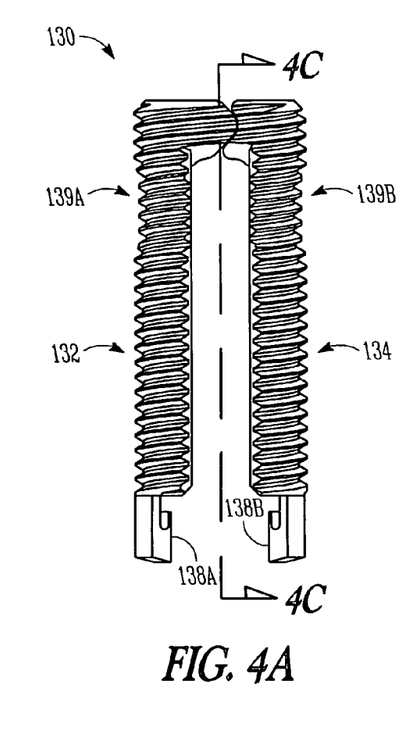
FIGS. 4A, 4B, and 4C illustrate a front elevational view, a cross-sectional view taken directly into the page of FIG. 4A, and a cross-sectional view taken along line 4C-4C of FIG. 4A, respectively, of a threaded tube element of the miniature rod reducer instrument of FIG. 1.
Figure 4B:
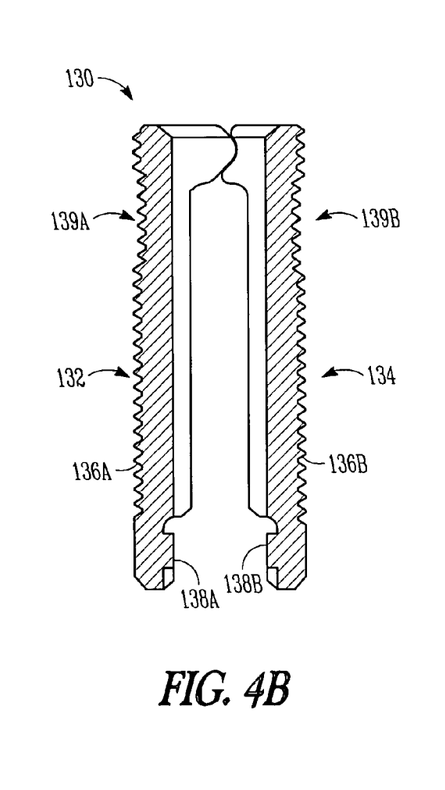
Figure 4C:
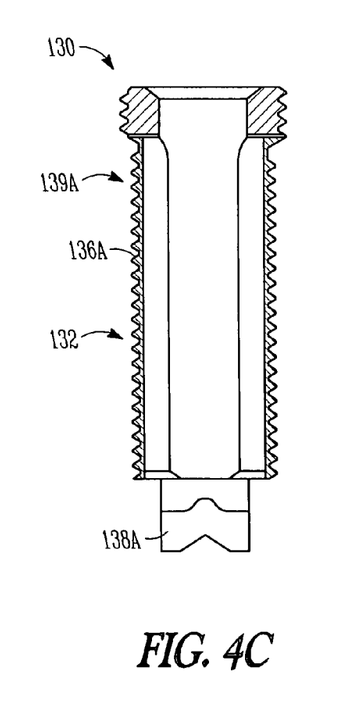
Figure 5A:
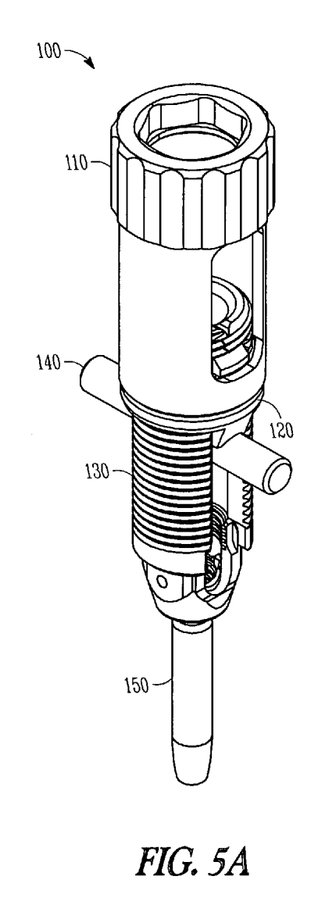
FIGS. 5A and 5B illustrate front perspective views of the miniature rod reducer instrument of FIG. 1 coupled to a spinal rod and a pedicle screw assembly in an unreduced and reduced rod configuration, respectively.
Figure 5B:
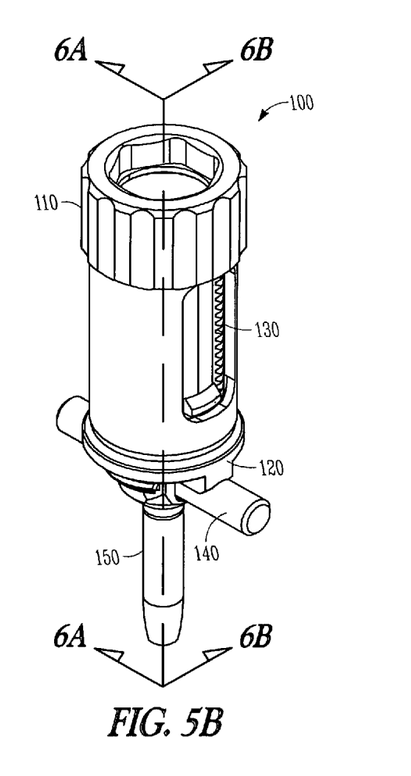

In an example, the retaining guide ring 120 is disposed around the threaded tube 130 at the distal end of the outer drive sleeve 110 and includes first and second upwardly extending arms 122A, 122B, first and second outwardly extending tabs 124A, 124B disposed on ends of the upwardly extending arms 122A, 122B, respectively, and a rod recess 126 disposed at the distal end of the retaining guide ring 120 that selectively interfaces with the spinal rod 140.

In an example, the outer drive sleeve 110 is constructed of stainless steel, titanium, or other biocompatible surgical grade metal, while the retaining guide ring 120 and threaded tube 130 are constructed of a biocompatible polymer material such as polyetheretherketone (PEEK). However, the drive sleeve 110 is not limited to metallic constructions and the retaining guide ring 120 and the threaded tube 130 are not limited to polymeric constructions and each may be constructed of any biocompatible material that is able to take on the general shape and withstand the normal operating conditions of the components. For example, the retaining guide ring 120 and threaded tube 130 may be constructed of titanium and the drive sleeve 110 may be constructed of PEEK.

In operation, and in continuing reference to FIGS. 1-7, a pedicle screw or several pedicle screw assemblies 150 are implanted into the vertebrae of a patient and the rod 140 may be pre-bent for potential deformity correction. The spinal rod 140 is loosely placed above the construct of pedicle screws 150 and attached to the pedicle screws 150 in which no reduction is necessary. The gripping surface 112 of the outer drive sleeve 110 is engaged and rotated with respect to the threaded tube 130 using manual rotation and/or the outer drive sleeve 110 may be rotated using the ratcheting T-handle driver instrument with a hex drive coupler 160 via the drive surface 116. The retaining guide ring 120 surrounds the features 139A, 139B such that the distal ends of the first and second legs 132, 134 splay open. The distal end of the rod reducer 100 is placed over the spinal rod 140 and above a pedicle screw assembly 150 such that the first and second legs 132, 134 straddle the rod 140 and the engagement features 138A, 138B surround the corresponding receptacles on the pedicle screw assembly 150. The outer drive sleeve 110 is then rotated manually with respect to the threaded tube 130 via the gripping surface 112 and/or rotating the ratcheting T-handle driver instrument with a hex drive coupler 160 with such that the retaining guide ring 120 and the outer drive sleeve 110 travel distally with respect to the threaded tube 130 via the engagement of the interior threading 118 and the first and second exterior threading 136A, 136B, thereby causing the unsplaying of the distal ends of the first and second arms 132, 134, engagement of the first and second engagement features 138A, 138B with the receptacles on the pedicle screw 150, engagement of the rod recess 126 to the spinal rod 140, and downward translation of the spinal rod 140 with respect to the first and second legs 132, 134. A plurality of rod reducer instruments 100 can be utilized in this manner to gradually reduce the spinal rod 140 into a plurality of pedicle screw assemblies 150 over a plurality of spinal levels. The rod reducers 100, in an example, are slowly and systematically actuated to avoid overstressing the pedicle screw assemblies 150 and the interface with their corresponding vertebral bodies, which further allows for gradual stressing and stretching of soft tissue of the patient's spine while potentially correcting a deformity. The ratcheting T-handle driver instrument with a hex drive coupler 160 is then uncoupled from the outer drive sleeve 110 and locking caps, elements which serve to finally secure the spinal rod 140 with respect to the pedicle screw assemblies 150, are introduced through the rod reducers 100 via a locking cap channel provided by the interior geometry of the threaded tube 130. The locking caps can be coupled to the pedicle screw assemblies 150 using a cap driver instrument (not shown), which can be inserted through the rod reducer 100. The locking cap driver 160 has an engagement feature for coupling to the locking caps and actuating their coupling to the pedicle screw assemblies 150, such as a threaded, star drive, or hex drive engagement feature. The locking cap driver 160 may be a ratcheting driver, but is not so limited. In an example, the locking caps are coupled to the pedicle screw assemblies 150 and the locking cap driver 160 is uncoupled from the rod reducers 100. The rod reducer(s) 100 are uncoupled from the pedicle screw assemblies 150 by disposing the retaining guide ring 120 over the features 139A, 139B such that the distal ends of the arms 132, 134 are splayed open and the engagement features 138A, 138B are disengaged from their corresponding receptacles on the pedicle screw assembly(s) 150. The rod reducer 100 can be cleaned and sterilized for reuse.

In some examples, the rod reducer 100 does not introduce notches or mar the exterior of the spinal rod 140 during its reduction. In addition, the rod reducer 100 of some examples prevents splaying of the upwardly extending arms that form the rod-receiving channel of the pedicle screw assembly 150.

The rod reducer 100 can be coupled to a pedicle screw assembly 150 prior to or subsequent to the implantation of the pedicle screw 150, according to surgeon preference. The rod reducer 100 can further be utilized to aid in de-rotation maneuvers of the spine during surgery.

In an example, and in reference to FIGS. 8A-8D, a rod reducer 200 is provided that is configured especially for coupling to a monoaxial pedicle screw 250 and reducing a spinal rod 140 thereto. In an example, the rod reducer 200 includes a threaded shaft 210 terminating distally in a grasping element 220 for coupling to the underside of the distal end of a monoaxial pedicle screw assembly 250. The rod reducer 200 further includes a nut 230 configured to interface with the exterior threading of the shaft 210 and threadedly translate with respect thereto. A claw element 240 having one or more arms, in an example, is coupled to the shaft 210 below the nut 230 and the one or more arms, in a further example, have a rod recess 242 for engaging the spinal rod 140.

In operation, and in continuing reference to FIGS. 8A-8D, the grasping element 220 is placed under a monoaxial pedicle screw 250. The claw element 240 engages the proximal side of the spinal rod and the nut 230 is rotated to force the claw element 240 to reduce the rod 140 via the rod recess 242 into the monoaxial pedicle screw assembly 250. A locking cap is coupled to the monoaxial pedicle screw assembly 250 and the rod reducer 200 is decoupled from the monoaxial pedicle screw assembly 250 by loosening the nut 230 and disengaging the claw 240 from the spinal rod 140.

In an example, and in reference to FIGS. 9A-9F, a rod reducer 300 is provided that includes a hex nut 310, a threaded tube 330 having a first leg 332 and a second leg 334, and a retaining guide ring 320. In an example, the rod reducer 300 is similar in function and operation to the rod reducer 100 with the exception that instead of the outer drive sleeve 110, the hex nut 310 is included and functions in conjunction with a hex socket type instrument (not shown) to actuate the rod reducer 300. The threaded tube 330 is similar in function and operation to the threaded tube 130 but incorporates a hinge design at the proximal end to control the splaying of the first and second legs 332, 334.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

The above Detailed Description includes references to the accompanying drawings, which form a part of the Detailed Description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more features thereof) may be used in combination with each other. Other embodiments can be used, such as by one of ordinary skill in the art upon reviewing the above description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The Abstract is provided to allow the reader to quickly ascertain the nature of the technical disclosure. It is submitted with the understanding that it will not be used to interpret or limit the scope or meaning of the claims.

What is claimed is:

1. A spinal rod reduction system comprising:
    a rod reducer including:
        a tubular first threaded member comprising a proximal end and a distal end spaced in a distal direction from the proximal end, and defining an outer surface, the tubular first threaded member including a first threaded portion extending along the outer surface in a proximal portion of the tubular first threaded member and a second threaded portion extending from the first threaded portion along the outer surface in the distal direction substantially along a remainder of the outer surface toward the distal end, wherein the tubular first threaded member further includes an engagement feature configured to selectively anchor the tubular first threaded member to a pedicle screw, a threaded first leg, and a threaded second leg, wherein proximal ends of the first and second legs are selectively rotatable with respect to one another to allow distal ends of the first and second legs to be selectively separable, and in at least one spacing of the distal ends of the first and second legs, a first outer thread diameter of the first threaded portion is less than a second outer thread diameter of the second threaded portion;
        a second threaded member defining an inner surface and including second threads around at least a portion of the inner surface, the second threads of the second threaded member configured to threadably engage with the first and second threaded portions of the tubular first threaded member, the second threaded member being movable along the tubular first threaded member with rotation of the second threaded member relative to the tubular first threaded member; and
        a spinal rod urging member connected to a distal end portion of the second threaded member and movable with the second threaded member as the second threaded member moves along the tubular first threaded member, the urging member including a concave bearing surface located at a distal end of the spinal rod urging member that is configured to abut a spinal rod,
    wherein, when the second threaded member is threadedly engaged with the tubular first threaded member and threadedly moved distally along the outer surface of the tubular first threaded member, the distal ends of the first and second legs move towards each other to decrease a distance between the distal ends of the first and second legs and the bearing surface of the spinal rod urging member is advanced adjacent the distal end of the tubular first threaded member.

2. The system of claim 1, wherein the second threaded member includes a tool engagement portion configured to engage with a tool configured to rotate the second threaded member with respect to the tubular first thread member.

3. The system of claim 2, wherein the tool engagement portion includes a recess including a drive surface configured to mate with the tool.

4. The system of claim 2, wherein the tool engagement portion includes a nut configured to mate with the tool.

5. The system of claim 4, wherein the nut includes a hex nut.

6. The system of claim 1, wherein the spinal rod urging member includes a claw element including one or more arms, each arm including the bearing surface configured to selectively abut the spinal rod.

7. The system of claim 6, wherein the bearing surface of each arm is disposed at an end of the arm.

8. The system of claim 6, wherein the bearing surface includes a rod recess.

9. The spinal rod reduction system of claim 1, further comprising
    a spinal rod;
    a plurality of pedicle screws configured to engage with the spinal rod; and
    a plurality of the rod reducers.

10. The spinal rod reduction system of claim 9, wherein the plurality of rod reducers are configured to engage with the pedicle screws and the spinal rod at locations where the spinal rod is spaced from the pedicle screws.

11. The spinal rod reduction system of claim 10, wherein the plurality of rod reducers are configured to incrementally urge the spinal rod toward the plurality of pedicle screws.

12. The spinal rod reduction system of claim 10, comprising a locking cap configured to engage with the pedicle screw and retain the spinal rod in engagement with the pedicle screw.

13. The spinal rod reduction system of claim 1, comprising a tool configured to mate with a tool engagement portion of each of the rod reducer, the tool being configured to rotate the second threaded member with respect to the tubular first thread member.

14. The spinal rod reduction system of claim 13, wherein the tool engagement portion includes a recess including a drive surface configured to mate with the tool.

15. The spinal rod reduction system of claim 13, wherein the tool engagement portion includes a nut configured to mate with the tool.

16. The system of claim 1, wherein the first and second legs are substantially semi-circular in cross section.

17. The system of claim 16, wherein the first and second legs of the tubular first threaded member are held together by the second threaded member threadably engaged around the outer surface of the tubular first threaded member.

18. The system of claim 1, wherein the first threaded member includes a gap between the first leg and the second leg, the gap being configured to accommodate the spinal rod.

19. The system of claim 18, wherein the bearing surface of the urging member is disposed at least partially within the gap between the first leg and the second leg.

20. The system of claim 1, wherein the engagement feature includes at least one protrusion configured to mate with a corresponding number of receptacles of an implantable screw assembly.

21. The system of claim 1, wherein the engagement feature includes a grasping element configured to selectively couple to a proximal end of an implantable screw assembly.

22. The system of claim 1, wherein the engagement feature is disposed at a distal end of the first threaded member.

23. The system of claim 1, wherein the urging member is coupled to the second threaded member.

24. The system of claim 1, wherein the engagement feature of the first threaded member includes a grasping element configured to couple to an underside of a head of an implantable screw assembly.

25. The system of claim 1, wherein the second threaded member includes a gripping surface configured to grip during manual rotation of the second threaded member with respect to the tubular first threaded member.

26. A spinal rod reduction system comprising:
a rod reducer including:
a first threaded member including a first threaded leg and a second threaded leg, each of the first and second threaded legs comprising a proximal end, a distal end spaced from the proximal end in a distal direction, an outer surface extending from the proximal end to the distal end, and external threading extending along the outer surface, wherein the distal end of each of the first and second threaded legs includes an engagement feature configured to selectively anchor the first threaded member to a pedicle screw, and the proximal end of each of the first and second threaded legs defines an abutment surface, the abutment surfaces configured to abut one another so as to allow the distal ends of the first and second threaded legs to splay open relative to one another;
a second threaded member defining an inner surface and including internal threading around at least a portion of the inner surface, the internal threading configured to threadably engage with the external threading of the first and second threaded legs, the second threaded member being movable along the first threaded member with rotation of the second threaded member relative to the first threaded member; and
a spinal rod urging member coupled to a distal end portion of the second threaded member and movable with the second threaded member as the second threaded member moves along the first threaded member, the spinal rod urging member including a bearing surface located at a distal end of the spinal rod urging member that is configured to abut a spinal rod,
wherein, when the second threaded member is threadedly engaged with the first threaded member and threadedly moved distally along the outer surfaces of the first and second threaded legs, the distal ends of the first and second threaded legs move towards each other to decrease a distance between the distal ends of the first and second threaded legs, and the bearing surface of the spinal rod urging member is advanced toward the distal ends of the first and second threaded legs.

27. The spinal rod reduction system of claim 26, wherein the external threading of each of the first and second threaded legs includes a first threading portion and a second threading portion extending in the distal direction from the first threading portion, and for each of the first and second threaded legs, the first threading portion includes a crest that extends to a first radial distance and the second threading portion includes a crest that extends a second radial distance, wherein the first radial distance is less than the second radial distance.

28. The spinal rod reduction system of claim 26, wherein the external threading of the first threaded leg extends in the distal direction with respect to the abutment surface of the first threaded leg, and the external threading of the second threaded leg extends in the distal direction with respect to the abutment surface of the second threaded leg.

29. The spinal rod reduction system of claim 26, wherein, when the second threaded member is threadedly engaged with the first threaded member and threadedly moved distally along the outer surfaces of the first and second threaded legs, threaded portions of the first and second threaded legs move toward each other to decrease a distance between the threaded portions of the first and second threaded legs.

30. The spinal rod reduction system of claim 26, wherein the abutment surfaces of the first and second threaded legs of the first threaded member are held together by the second threaded member threadably engaged around the outer surfaces of the first and second threaded legs.

31. The spinal rod reduction system of claim 26, wherein a threaded portion of the first threaded leg is spaced from a threaded portion of the second threaded leg so as to define a gap that extends entirely through the first threaded member between the threaded portions of the first and second threaded legs.

32. A spinal rod reduction system, comprising:
a rod reducer comprising:
(a) a first tubular member comprising a proximal end, a distal end, an outer surface having a length, and external threads extending from the proximal end substantially along the length of the outer surface toward the distal end, the first tubular member further comprising first and second threaded legs having distal portions that are selectively separable from one another, wherein a first threaded portion located in a proximal portion of the outer surface has a first outer thread diameter in at least one spacing of the first and second threaded legs and a second threaded portion located distally from the first threaded portion on the outer surface has a second outer thread diameter in the at least one spacing of the first and second threaded legs, where the second outer thread diameter is greater than the first outer thread diameter;

(b) an outer drive sleeve defining an inner surface and including a third threaded portion on the inner surface, the third threaded portion dimensioned to threadingly engage the first and second threaded portions of the first tubular member; and (c) a spinal rod urging member connected to the outer drive sleeve at a distal end portion of the outer drive sleeve, the spinal rod urging member comprising a concave bearing surface configured to abut a spinal rod, wherein when the outer drive sleeve is threadingly engaged with the first or second threaded portions of the first tubular member, the outer drive sleeve and spinal rod urging member are axially movable along the outer surface of the first tubular member with rotation of the outer drive sleeve relative to the first tubular member;

wherein when the outer drive sleeve is threadingly engaged with the first threaded portion of the first tubular member and axially advanced along the outer surface of the first tubular member to the second threaded portion, a distance between the distal portions of the first threaded leg and the second threaded leg is reduced and the bearing surface of the spinal rod urging member is advanced to a location adjacent the distal end of the first tubular member.

33. The spinal rod reduction system of claim 32 wherein the first threaded leg and the second threaded leg are separate components held together by the outer drive sleeve.

\* \* \* \* \*